US008217199B2

(12) United States Patent
Chung et al.

(10) Patent No.: US 8,217,199 B2
(45) Date of Patent: Jul. 10, 2012

(54) STABLE WATER SOLUBLE COMPOSITION CONTAINING LYSOPHOSPHATIDYLETHANOLAMINE AND LECITHIN

(75) Inventors: Guk Hoon Chung, Seongnam-si (KR); Ji Heun Hong, Yongin-si (KR); Young Lae Yang, Yongin-si (KR)

(73) Assignee: Doosan Corporation, Seoul (KR)

( * ) Notice: Subject to any disclaimer, the term of this patent is extended or adjusted under 35 U.S.C. 154(b) by 252 days.

(21) Appl. No.: 11/994,259

(22) PCT Filed: Jun. 30, 2006

(86) PCT No.: PCT/KR2006/002570
§ 371 (c)(1),
(2), (4) Date: Mar. 18, 2008

(87) PCT Pub. No.: WO2007/004823
PCT Pub. Date: Jan. 11, 2007

(65) Prior Publication Data
US 2008/0188683 A1    Aug. 7, 2008

(30) Foreign Application Priority Data

Jun. 30, 2005  (KR) .................. 10-2005-0058063
Jun. 29, 2006  (KR) .................. 10-2006-0059487

(51) Int. Cl.
*C07F 9/02* (2006.01)
*A01N 57/02* (2006.01)
*C08K 5/00* (2006.01)

(52) U.S. Cl. .......... 564/15; 504/201; 504/206; 524/140; 524/145; 554/79; 554/80; 554/1; 554/10

(58) Field of Classification Search .................. 435/128; 564/15; 504/201, 206; 524/140, 145; 554/1, 554/10
See application file for complete search history.

(56) References Cited

U.S. PATENT DOCUMENTS

| 4,681,617 | A | * | 7/1987 | Ghyczy et al. ............ 504/206 |
| 5,110,341 | A | | 5/1992 | Palta et al. |
| 5,126,155 | A | | 6/1992 | Palta et al. |
| 6,610,313 | B2 | | 8/2003 | Chung et al. |
| 6,773,902 | B1 | * | 8/2004 | Chung et al. ............. 435/128 |

(Continued)

FOREIGN PATENT DOCUMENTS

CN    7105517 A    5/1988

(Continued)

OTHER PUBLICATIONS

Ramadan et al., "Oil composition of coriander (*Coriandrum sativum* L.) fruit-seeds." *eur Food Res Technol* 215(2002): 204-209.

Farag et al., "Stimulation of ethylene production by urea, thidiazuron, and lysophosphatidylethanolamine and possible sites of this stimulation . . ." *Annual meeting of the American Society of Plant Physiologists* (Apr. 1989): 95.

(Continued)

*Primary Examiner* — Yate K Cutliff
(74) *Attorney, Agent, or Firm* — Merchant & Gould P.C.

(57) ABSTRACT

The invention relates to a stable water soluble composition containing lithophosphatidylethanol amine (LPE) or lecithin including the LPE 3% or more. The composition comprises one or both of lysophosphatidylethanol amine and lecithin 0.1 to 50 wt %, fatty acid or salt thereof 0.1 to 60 wt % and solvent 10 to 99.8 wt %. According to the invention, it is possible to provide the stable water soluble composition of lithophosphatidylethanolamine and lecithin which does not cause the precipitation at the room temperature below 20° C. and can maintain the clear formulation even during the long term keeping.

6 Claims, 1 Drawing Sheet

U.S. PATENT DOCUMENTS

2006/0228458 A1 * 10/2006 Sardo .......................... 426/601

FOREIGN PATENT DOCUMENTS

| CN | 1176655 A | 3/1998 |
| --- | --- | --- |
| JP | 63-279753 | 11/1994 |
| WO | WO 01/40496 A1 | 6/2001 |
| WO | WO 03/019263 A1 | 4/2003 |
| WO | WO2004091301 | * 10/2004 |

OTHER PUBLICATIONS

Kaur et al., "Postharvest dip in a natural lipid, lysotphosphatidylethanolamine, may prolong vase life of Snap Dragon flowers." *Hortscience* 32:5(1997): 888-890.

* cited by examiner

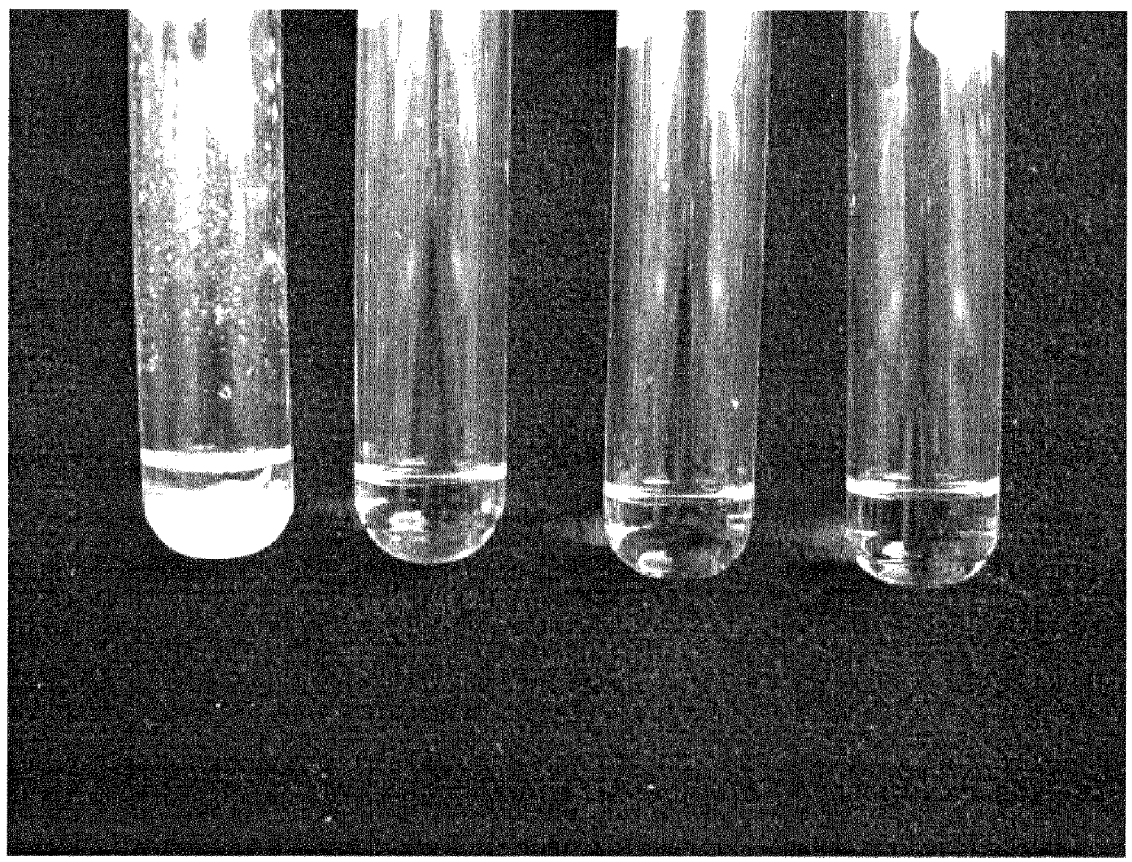

STABLE WATER SOLUBLE COMPOSITION CONTAINING LYSOPHOSPHATIDYLETHANOLAMINE AND LECITHIN

TECHNICAL FIELD

The invention relates to a stable water soluble formulation of lysophosphatidylethanolamine.

BACKGROUND ART

Lysophosphatidylethanolamine naturally exists in cells of plants and animals, and is particularly much contained in yolks or brain cells. The lysophosphatidylethanolamine is derived from phosphatidylethanolamine which is a kind of phospholipids found in a cell membrane. The phosphatidylethanolamine plentiful in the yolk or soybean lecithin is a kind of the phospholipids and contains two fatty acids in a molecule thereof. In a living body, the phosphatidylethanolamine is subject to an action of phospholipase A2 action, which is hydrolase of the phospholipids, so that one fatty acid located at a sn-2 position is removed. As a result, the phosphatidylethanolamine is converted into lysophosphatidylethanolamine.

The lysophosphatidylethanolamine is known that it plays an important role in ripening and senescence of fruits. It is known that treatment of the lysophosphatidylethanolamine suppresses the ripening of leaves of a tomato and the fruit. In addition, it is also known that the treatment of lysophosphatidylethanolamine after the harvest of tomato extends a storage period of the fruit (U.S. Pat. Nos. 5,110,341 and 5,126,155). Further, it is also known that the treatment of the lysophosphatidylethanolamine to apples promotes formation of anthocyanine in the skin and suppresses loss of firmness during the storage of the apples harvested. It is known that these actions are related to functions of lowering a respiration rate of the fruit such as apple, cranberry and tomato and promoting or suppressing a formation of ethylene gas (Farag, K. M. and J. P. Palta, "Stimulation of Ethylene Production by Erea, Thidiazoron, and Lysophosphatidylethanolamine and Possible sites of this stimulation" Annual meeting of the American Society of Plant Physiologists, April 1989).

A solution of lysophosphatidylethanolamine which is adjusted to have a proper concentration is used as means for prolonging a lifetime of a cut flower (HortScience 32(5): 888-890, 1997). In general, since treatment of a silver thiosulfate solution containing sugar to a harvested flower about for 20 hours or more suppresses the senescence of the flower, it has been used for such uses up to recently. However, since silver ions contained in the solution cause environmental pollutions, the use of the solution is avoided in U.S recently. The lysophosphatidylethanolamine which is purified from nature sources is known to improve the storage ability of the cut flower in a vase, as the sliver thiosulfate solution. Accordingly, it is actively driven the use of the lysophosphatidylethanolamine in the related fields.

As described above, the lysophosphatidylethanolamine is very usefully used in an agriculture field. However, it is difficult to keep and maintain the stable formulation thereof in an aqueous solution. In case of a 10% aqueous solution of lysophosphatidylethanolamine, which is currently commercialized, there occurs precipitation at temperatures below about 20° C., so that the formulation thereof becomes unstable. In addition, when it is kept for a long time, there occurs precipitation. Further, when the lysophosphatidylethanolamine is diluted in water just before it is applied to the crops, since it is not stably dissolved, it cannot be effectively used. Additionally, there occurs a problem in the external appearance thereof as a product when it is put on the market.

DISCLOSURE

Technical Problem

An object of an embodiment of the invention is to provide a stable water-soluble composition of lysophosphatidylethanolamine or lecithin. More specifically, the object of an embodiment of the invention is to provide a stable water-soluble composition of lysophosphatidylethanolamine or lecithin which does not cause the precipitation at the room temperature below 20° C. and can maintain a clear formulation thereof even for a long storage time.

Technical Solution

In order to achieve the above object, there is provided a water soluble composition containing LPE or lecithin, the composition comprising one or both of lysophosphatidylethanolamine and lecithin 0.1 to 50 wt %, fatty acid or salt thereof 0.1 to 60 wt % and solvent 10 to 99.8 wt %.

According to a preferred embodiment of the invention, the lecithin is lecithin containing 3% or more of LPE, more preferably 5% or more.

According to a preferred embodiment of the invention, the lecithin is modified lecithin selected from a group consisting of hydroxylated lecithin, acetylated lecithin and enzyme-treated lecithin.

According to a preferred embodiment of the invention, the enzyme is phospholipase.

According to a preferred embodiment of the invention, the LPE is hydrogenated LPE.

According to a preferred embodiment of the invention, the fatty acid is natural or synthesized fatty acid having a carbon number of 3~22, preferably 6~14.

According to a preferred embodiment of the invention, the salt of the fatty acid is one or more selected from a group consisting of sodium salt, potassium salt, ammonium salt and ethanol amine salt.

According to a preferred embodiment of the invention, the solvent is a mixing solvent of water and alcohol.

According to a preferred embodiment of the invention, the alcohol is at least one selected from a group consisting of ethanol, isopropanol, butanol, hexanol and oleyl alcohol.

According to a preferred embodiment of the invention, the alcohol consists of ethanol or isopropanol, butanol, hexanol and oleyl alcohol.

According to a preferred embodiment of the invention, a volume ratio of water, ethanol or isopropanol, butanol, hexanol and oleyl alcohol is 0.4~4.0:0.2~2.0:0.2~2.0:0.2~2.0: 0.1~1.0.

ADVANTAGEOUS EFFECTS

When the water soluble composition containing LPE or lecithin including LPE is used, it is possible to provide a stable water soluble composition of lysophosphatidylethanolamine or lecithin containing lysophosphatidylethanolamine, which does not cause precipitation at the room temperature below 20° C. and can maintain a clear formulation thereof even during the long time keeping.

DESCRIPTION OF DRAWINGS

FIG. 1 is a photograph comparing stabilities of a water soluble compositing containing LPE according to an embodiment of the invention and that of a comparative example.

BEST MODE

In the followings, it will be more specifically described a stable water soluble composition containing lysophosphatidylethanolamine or lecithin including the lysophosphatidylethanolamine, according to the invention.

Solutes of the water soluble composition of the invention are lysophosphatidylethanolamine (LPE), lecithin including LPE, and fatty acid or salts thereof, etc.

Since the LPE naturally exists in cells of plants and animals, the one refined from the nature can be used as the LPE. In particular, it can be extracted from lecithin of soybean, yolk or rape seed production. Crude soybean lecithin (often referred to as crude lecithin) which is produced as a by-product during the production of soybean milk consists of polar lipid (phospholipid/glycolipid) 60~70%, soybean 27~39%, water 1~3% and the other substances 0.5~3.0%. Among them, the polar lipid is refined by removing the soybean milk which is neutral lipid contained in the crude lecithin, and is defined as soybean lecithin. The lecithin composition refined consists of phosphatidylcholine (PC) 22~30%, lysophosphatidylcholine (LPC) 2~5%, phosphatidylethanolamine (PE) 16~22%, lysophosphatidylethanolamine 0.5~2%, phosphatidic acid (PA) 0.5~8%, phosphatidyl serine 0.1~3%, phosphatidylinositol 6~15% and balances. The yolk lecithin also consists of phosphatidylcholine (PC) 73~83%, lysophosphatidylcholine (LPC) 2~5%, phosphatidylethanolamine (PE) 13~17%, lysophosphatidylethanolamine (LPE) 1~3% and balances. Like this, since the lecithin contains a very little amount of lysophosphatidylethanolamine, it is difficult to directly isolate and to use the lysophosphatidylethanolamine from the lecithin. Accordingly, it is possible to use lysophosphatidylethanolamine produced by reacting the lecithin with ethanolamine under presence of phospholipase D and phospholipase A. In addition, hydrogenated lysophosphatidylethanolamine can be used. Further, it is possible to use lysophosphatidylethanolamine obtained by hydrolyzing phosphatidylethanolamine, which is extracted from the nature, into lysophosphatidylethanolamine, or modifying phosphatidylcholine into phosphatidylethanolamine and then hydrolyzing it into lysophosphatidylethanolamine.

According to the invention, the lecithin is preferably lecithin containing 3% or more LPE, more preferably 5% or more. When the content of LPE in the lecithin is below 3%, it is difficult to obtain a stable water soluble formulation.

In addition, the lecithin itself containing a small amount of LPE can be used as it is. However, as described above, the normal soybean lecithin contains a very small amount of LPE. Accordingly, it is possible to enrich LPE in the lecithin by a refining process or arbitrary chemical or biochemical treatment and then to use it for the invention. For example, it is possible to obtain modified soybean lecithin in which the LPE is enriched by treating the soybean lecithin with snake venom phospholipase A2, pancreatic phospholipase A2 or neutral lipase, and then to use the obtained lecithin for the invention. As a typical example, there is enzyme modified soybean lecithin available from Solae company. As another lecithin which can be used for the invention, there is hydroxylated soybean lecithin or acetylated soybean lecithin. The hydroxylated soybean lecithin is lecithin made to include a hydroxyl group in a double bond of fatty acid, which is contained in the lecithin, by chemically treating the refined soybean lecithin or crude soybean lecithin before the refining. This can be used for the invention as it is. Alternatively, it is possible to enrich a large amount of LPE in the hydroxylated soybean lecithin by treating it with phospholipase enzyme and then to use it. The acetylated soybean lecithin is lecithin made to include a acetyl group in an amine group, which is contained in the lecithin, by chemically treating the refined soybean lecithin or crude soybean lecithin before the refining. This can be used for the invention as it is. Alternatively, it is possible to enrich a large amount of LPE in the acetylated soybean lecithin by treating it with phospholipase enzyme and then to use it.

The fatty acid having a carbon number 3~22 can be used for the invention. Saturated fatty acid having no double bond or unsaturated fatty acid having one or more double bonds in a middle of the fatty acid can be used for the invention. Examples of the saturated fatty acids include propionic acid, butanoic acid such as butyric acid, peptanoic acid such as valeric acid, hexanoic acid such as caproic acid, heptanoic acid, octanoic acid such as caprylic acid, decanoic acid such as capric acid, undecanoic acid, dodecanoic acid such as lauric acid, tridecanoic acid, tetradecanoic acid such as myristic acid, pentadecanoic acid, hexadecanoic acid such as palmitic acid, heptadecanoic acid such as margaric acid, octadecanoic acid such as stearic acid, nonadecanoic acid, icosanoic acid such as arachidic acid, henicosanoic acid, docosanoic acid such as behenic acid, tricosanoic acid, tetracosanoic acid such as lignoceric acid and the like. Examples of the unsaturated fatty acid having one double bond in the saturated fatty acids include hexenoic acid, octenoic acid, decenoic acid, dodecenoic acid, tetradecenoic acid, hexadecenoic acid such as palmitoleic acid, octadecenoic acid such as oleic acid and petroselinic acid, docosenoic acid such as erucic acid, and the like. Further, it can be used linoleic acid, linolenic acid, arachidonic acid, docodapentaenoic acid and the like having two or more double bonds. However, considering that the plant surface is very non-polar and in order for an effective substance to penetrate the plant surface or to attach to the plant surface very well, it can be used the fatty acid having a carbon number of 8~14, more preferably 8~12 and most preferably 10~12.

Although the salt of the fatty acid is not particularly limited, it is preferably selected from sodium salt, potassium salt, ammonium salt and ethanol amine salt. The ethanol amine salt may be one of monoethanol amine salt, diethanol amine salt and triethanol amine salt.

LPE and lecithin containing LPE can be included in the amount of 0.1~50 wt % of the total composition. Preferably, the content of LPE or lecithin containing LPE is 1~25 wt %, more preferably 5~20 wt % and even more preferably 8~12 wt %. The most preferred content of LPE or lecithin containing LPE is about 10 wt %. When the contents of LPE and lecithin containing LPE are included in the range, the stability of the composition of water soluble formulation is significantly improved.

The fatty acid or salts thereof can be included in an amount of 0.1~60 wt % of the total composition. Preferably, the content of fatty acid or salts thereof is 1~25 wt % of the total composition, more preferably 5~20 wt %. The most preferred content of the fatty acid or salts thereof is about 10 wt %. When the content of the fatty acid or salts thereof is included in the range, it enables LPE or lecithin containing LPE to be dissolved in the aqueous solution well, thereby maintaining the stable formulation.

The solvent of the water soluble composition of the invention is preferably a mixing solvent of water and alcohol. The content of solvent is 10~99.8 wt % of the total composition. The preferred content of solvent is 50~99.8 wt % of the total composition. The more preferred content of solvent is 76~84 wt %. When the content of solvent is included in the range, the solubility of LPE or lecithin containing LPE is increased.

Herein, water is essential solvent. The alcohol is preferably at least one of selected from a group consisting of ethanol, isopropanol, butanol, hexanol and oleyl alcohol. Among them, particularly, it is preferable alcohol consisting of ethanol or isopropanol, butanol, hexanol and oleyl alcohol.

A volume ratio of water, ethanol or isopropanol, buthanol, hexanol and oleyl alcohol is preferably 0.4~4.0:0.2~2.0:0.2~2.0:0.2~2.0:0.1~1.0, and more preferably 1.6~2.4:0.8~1.2:0.8~1.2:0.8~1.2:0.4~0.6. The most preferred ratio is about 2:about 1:about 1:about 1:about 0.5. When the ratio is included in the range, it is possible to stably maintain the water soluble composition formulation of LPE or lecithin containing LPE.

In the specification including claims, the term of "water soluble" of the "water soluble composition containing LPE or lecithin containing LPE" has the widest meaning. That is, the "water soluble" comprises the meaning that LPE or lecithin containing the LPE is clearly and stably dissolved in the solvent including water, without precipitation. Further, the "water soluble" comprises the meaning that when the "water soluble composition containing LPE or lecithin containing LPE" is diluted in water to use it, the water soluble composition of LPE or lecithin containing LPE is clearly and stably diluted in the water without precipitation.

Mode for Invention

Hereinafter, the invention will be more specifically described with reference to examples. However, the examples are provided to illustrate the invention, not to limit it.

EXAMPLES

Production Example 1

Production of LPE

The refined yolk phospholipid DS-PL95E (Doosan Serdary Research Lab.; phosphatidylcholine 75%, phosphatidylethanolamine 14%, balances 11%) 30 g was dissolved in ethyl acetate 60 ml. The phospholipase D 800 unit (available from Sigma) originated from *Streptomyces* genus was mixed with 100 ml of sodium accetate (100 mM, pH 5.6) buffer solution containing 80 mM $CaCl_2$ and ethanolamine 8 g. Then, the mixed solution was mixed with the dissolved phospholipid solution and was reacted for 13 hours while stirring at 300 rpm, at 35° C. According to an analysis result of the reaction solution with HPLC, the content of phosphatidylethanolamine of phospholipid in the reaction solution was 79% and the content of phosphatidylcholine was 16%.

The solution was added with 3 ml of Lecitase (10,000 IU/ml, Novo Nordisk company) and violently stirred and reacted at 35° C. for 6 hours. 50 ml was extracted from the obtained reaction solution, put in a 250 ml of round flask, reduced pressure-evaporated at 40° C. with a rotary vacuum evaporator to remove ethyl acetate, which was solvent, treated with 100 ml of anhydrous ethanol, left alone at −2° C. for one hour and 30 minutes and then filtered. The obtained material filtered of 8.7 g was treated with 100 ml mixing solution of ethanol, ethyl acetate and water (=1:0.5:0.5, v/v/v), slowly stirred at 60° C. and then heated for 30 minutes. This solution was filtered to remove impurities and the remaining solution was cold-kept at −2° C. for 3 hours. The crystallized solution was filtered to obtain the filtered material of 4.8 g. The obtained material filtered was treated with 80 ml mixing solution of ethanol, ethyl acetate and water (=1:0.5:0.5, v/v/v), slowly stirred at 60° C., heated for 30 minutes, slowly cooled to −2° C. and then filtered. The filtered material was treated two times with the above solution in the same manner and vacuum-dried at 30° C. Then, according to an analysis result of the dried material with a liquid chromatography, it could be seen that 1.6 g of lisophosphatidylethanolamine having a phospholipid purity of 97% or more was obtained. The obtained LPE was used for following tests.

Production Example 2

Production of Modified Lecithin Containing LPE

The refined soybean lecithin (Central Soya; phosphatidylcholine 25%, phosphatidylethanolamine 20%, balances 11%) 30 g was dissolved in 90 ml of ethyl acetate. 80 mM $CaCl_2$ and 50 ml of sodium acetate (100 mM, pH 5.6) buffer solution were mixed. This mixed solution was mixed with the above dissolved phospholipid solution. This mixed solution was added with 3 ml of Lecitase (10,000 IU/ml, Novo Nordisk company) and reacted at 35° C. for 6 hours while stirring violently. Ethyl acetate of upper layer of the obtained reaction solution was removed and the contents were put in a 250 ml of round flask, reduced pressure-evaporated at 40° C. with a rotary vacuum evaporator to completely remove ethyl acetate, which was solvent, treated and dissolved with 200 ml of anhydrous ethanol, left alone at −2° C. for one hour and 30 minutes and then filtered. The obtained material filtered was treated with 20 ml of 80% ethanol, heated for melting, left along at a room temperature, treated with 200 ml of acetone for crystallization and then filtered. After vacuum drying at 30° C., according to an analysis result of the obtained material dried with a liquid chromatography, it could be seen that 0.9 g of modified lecithine containing lisophosphatidylethanolamine having a phospholipid purity of 20% or more was obtained. The obtained lecithin containing LPE was used for following tests.

Embodiment 1

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of sodium salt of decanoic acid having a carbon number of 10, and stirred at 2,000 rpm, thereby producing LPE 10% solution.

Embodiment 2

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of potassium salt of octanoic acid having a carbon number of 8, and stirred at 2,000 rpm, thereby producing LPE 10% solution.

Embodiment 3

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of monoethanol amine salt of lauric acid having a carbon number of 12, and stirred at 300 rpm, thereby producing LPE 10% solution.

Embodiment 4

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of ammonium salt of hexanoic acid having a carbon number of 6, and stirred at 1,000 rpm, thereby producing LPE 10% solution.

Embodiment 5

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of monoethanol amine salt of tetradecanoic acid having a carbon number of 14, and stirred at 500 rpm, thereby producing LPE 10% solution.

Embodiment 6

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of ethanol amine salt of butyric acid having a carbon number of 4, and stirred at 2,000 rpm, thereby producing LPE 10% solution.

Embodiment 7

The mixing solvent consisting of water 30 wt %, isopropanol 14 wt %, butanol 14 wt %, hexanol 14 wt % and oleyl alcohol 8 wt % was added with 10 wt % of the LPE produced in the production example 1 and 10 wt % of ethanol amine salt of oleic acid having a carbon number of 18 and one double bond, and stirred at 1,000 rpm, thereby producing LPE 10% solution.

Embodiment 8

The mixing solvent consisting of water 50 wt % and ethanol 40 wt % was added with 3 wt % of the lecithin produced in the production example 2, 4 wt % of ethanol amine salt of decanoic acid having a carbon number of 10 and 3 wt % of ethanol amine salt of oleic acid having a carbon number of 18 and one double bond, and stirred at 1,000 rpm, thereby producing lecithin 30% solution.

Embodiment 9

The mixing solvent consisting of water 30 wt %, isopropanol 14 wt %, butanol 14 wt %, hexanol 14 wt % and oleyl alcohol 13 wt % was added with 5 wt % of the lecithin produced in the production example 2, 5 wt % of ethanol amine salt of decanoic acid having a carbon number of 10 and 5 wt % of ethanol amine salt of oleic acid having a carbon number of 18 and one double bond, and stirred at 1,000 rpm, thereby producing lecithin 50% solution.

Comparative Example 1

The mixing solvent consisting of water 34 wt %, isopropanol 16 wt %, butanol 16 wt %, hexanol 16 wt % and oleyl alcohol 8 wt % was added with 10 wt % of the LPE produced in the production example 1, and stirred at 2,000 rpm, thereby producing LPE 10% solution.

Experimental Example

The respective solutions produced according to the embodiments 1 to 9 and comparative example 1 were observed with regard to the states just after the productions and then set at 18° C. for three days and then observed. As a result, the respective solutions of the embodiments 1 to 9 maintained the clear state since all the solutes were dissolved well just after the productions, and still maintained the clear state even after 3 days. Regarding the degree of clearness, the embodiments 1 to 3 were highest. On the contrary, in the solution of the comparative example 1, it was observed that the solutes, which were not dissolved even just after the stirring for the solution production, were attached to a wall of the receptacle and there occurred the precipitations 3 days later.

The result after 3 days can be seen from FIG. 1. The first solution of FIG. 1 is the solution of the comparative example 1, the second solution is the solution of the embodiment 1, the third solution is the solution of the embodiment 2 and the fourth solution is the solution of the embodiment 3. As shown in FIG. 1, it can be seen in the solution of the comparative example 1 that the solutes, which are not dissolved, are attached and precipitated to the inner wall and bottom of the receptacle. On the contrary, it can be seen that the solutions of the embodiments 1 to 3 maintain the clear state without the solutes attached or precipitated to the inner wall or bottom of the receptacle.

[Industrial Applicability]

When the water soluble composition containing LPE or lecithin including LPE is used, it is possible to provide the stable water soluble composition of lisophosphatidylethanolamine or lecithin containing lisophosphatidylethanolamine which is not precipitated at room temperatures below 20° C. and can maintain the clear formulation even during the long term storage.

The invention claimed is:

1. A water soluble composition containing lysophosphatidylethanolamine or lecithin, comprising:
   0.1 to 50 wt % of one or both of water-soluble lysophosphatidylethanolamine and lecithin,
   0.1 to 60 wt % of a fatty acid or a salt thereof, and
   10 to 99.8 wt % of a mixing solvent of water and alcohol, wherein the alcohol is at least one selected from a group consisting of ethanol, isopropanol, butanol, hexanol and oleyl alcohol, based on the total weight of the composition,
   wherein the lecithin contains 3% or more of lysophosphatidylethanolamine, based on the total weight of the lecithin, and
   wherein the water soluble composition containing lysophosphatidylethanolamine or lecithin maintains a clear formulation.

2. The composition according to claim 1, wherein the lysophosphatidylethanolamine is hydrogenated lysophosphatidylethanolamine.

3. The composition according to claim 1, wherein the composition comprises 5 to 20 wt % of one or both of lysophosphatidylethanolamine and lecithin, 5 to 20 wt % of a fatty acid or a salt thereof and 76 to 84 wt % of a mixing solvent of water and alcohol, based on the total weight of the composition.

4. The composition according to claim 1, wherein the alcohol consists of ethanol or isopropanol, butanol, hexanol and oleyl alcohol.

5. The composition according to claim 4, wherein a volume ratio of water:ethanol or isopropanol:butanol:hexanol:oleyl alcohol is 0.4~4.0:0.2~2.0:0.2~2.0:0.2~2.0:0.1~1.0.

6. The composition according to claim 5, wherein a volume ratio of water , ethanol or isopropanol, butanol, hexanol and oleyl alcohol is 1.6~2.4:0.8~1.2:0.8~1.2:0.8~1.2:0.4~0.6.

* * * * *